United States Patent [19]

Francoeur

[11] Patent Number: 5,270,167
[45] Date of Patent: * Dec. 14, 1993

[54] METHODS OF IDENTIFICATION EMPLOYING ANTIBODY PROFILES

[75] Inventor: Ann-Michele Francoeur, San Diego, Calif.

[73] Assignee: Dicor Technologies, Inc., Lake Forest, Calif.

[*] Notice: The portion of the term of this patent subsequent to Nov. 14, 2006 has been disclaimed.

[21] Appl. No.: 435,962

[22] Filed: Nov. 13, 1989

Related U.S. Application Data

[63] Continuation-in-part of Ser. No. 71,707, Jul. 9, 1987, Pat. No. 4,880,750.

[51] Int. Cl.⁵ .............. G01N 33/543; G01N 33/548; G01N 33/559
[52] U.S. Cl. .............. 435/7.21; 435/7.23; 435/7.24; 435/7.95; 436/501; 436/515; 436/518; 436/530; 436/548
[58] Field of Search .............. 435/7, 805, 810, 948, 435/7.21, 7.23, 7.24, 7.95; 436/501, 530, 548, 807, 808, 810, 828, 515, 518; 424/11; 935/110

[56] References Cited

U.S. PATENT DOCUMENTS

| | | | |
|---|---|---|---|
| 3,964,992 | 6/1976 | Krotz | 204/299 R |
| 3,988,230 | 10/1976 | Krotz | 204/180 G |
| 4,031,197 | 6/1977 | Marinkovich | 424/1 |
| 4,136,229 | 1/1979 | Godet et al. | 428/537 |
| 4,452,901 | 6/1984 | Gordon et al. | 436/506 |
| 4,471,056 | 9/1984 | Grommet et al. | 436/513 |
| 4,582,788 | 4/1986 | Erlich | 435/6 |
| 4,582,789 | 4/1986 | Sheldon, III et al. | 435/6 |
| 4,591,570 | 5/1986 | Chang | 436/518 |
| 4,608,246 | 8/1986 | Bayer et al. | 424/11 |
| 4,617,261 | 10/1986 | Sheldon, III et al. | 435/6 |
| 4,657,852 | 4/1987 | Grumet et al. | 435/7 |
| 4,708,931 | 11/1987 | Christian | 435/7 |
| 4,710,463 | 12/1987 | Murray | 435/68 |
| 4,713,349 | 12/1987 | Levin | 436/515 |
| 4,880,750 | 11/1989 | Francoeur | 436/530 |

FOREIGN PATENT DOCUMENTS

| | | |
|---|---|---|
| 1215304 | 12/1986 | Canada . |
| 0135108 | 8/1984 | European Pat. Off. . |
| 15702 | of 1897 | United Kingdom . |
| 2099578A | 5/1983 | United Kingdom . |
| 2135774A | 2/1984 | United Kingdom . |
| 2166445 | 10/1986 | United Kingdom . |
| 2166445B | 11/1987 | United Kingdom . |

OTHER PUBLICATIONS

Francoeue, *Biotechnology*, 6, 822-825, 1988.
Hales et al, *Meth. Enz.*, 70, 334-337, 1980.
Towbin et al, *Journ. Immunol. Meth.*, 72, 313-340, 1984.
"Leaving Holmes in the Dust," *Newsweek*, p. 81 (Oct. 26, 1987).
Wetton et al., "Demographic Study of a Wild House Sparrow Population by DNA Fingerprinting," *Nature* 327:147 (May 14, 1987).

(List continued on next page.)

*Primary Examiner*—David Saunders
*Attorney, Agent, or Firm*—Madson & Metcalf

[57] ABSTRACT

An identification method, applicable to the identification of animals or inanimate objects, is described. The method takes advantage of the set of individual-specific antibodies that are part of the unique antibody repertoire present in animals, by reacting an effective amount of such antibodies with a particular panel, of n-dimensional array (where n is typically one or two) consisting of an effective amount of many different antigens (typically greater than one thousand), to give antibody-antigen complexes. The profile or pattern formed by the antigen-antibody complexes, termed an antibody fingerprint, when revealed by an effective amount of an appropriate detector molecule, is uniquely representative of a particular individual. The method can similarly be used to distinguish genetically, or otherwise similar individuals, or their body parts containing individual-specific antibodies.

14 Claims, 11 Drawing Sheets

OTHER PUBLICATIONS

Nakamura et al., "Variable Number of Tandem Repeat Markers for Human Gene Mapping," Science 235:1616 (Mar. 27, 1987).

Gill et al., "Forensic Application of DNA Fingerprints," Nature 318:577 (Dec. 12, 1985).

Jeffreys et al., "Positive Identification of An Immigration Test-Case Using Human DNA Fingerprints," Nature 317:813 (Oct. 31, 1985).

Jeffreys et al., "Individual-Specific Fingerprints of Human DNA," Nature 316:76 (Jul. 4, 1985).

Francoeur et al., "Identification of Ki (Ku, p70/p80) Autoantigens and Analysis of Anti-Ki Autoantibody Reactivity", The Journal of Immunology 136:5 (Mar. 1, 1986).

Dighiero et al., "High Frequency of Natural Autoantibodies in Normal Newborn Mice," J. Immunol. 134:765–771 (1985).

Jeffreys et al., "Hypervariable 'Minisatellite' Regions In Human DNA," Nature 314:67 (Mar. 7, 1985).

Avrameas, "Natural Antibodies Against Tubulin, Actin, Myoglobin, Thyroglobulin, Retuin, Albuminum and Transferrin Are Present in Normal Sera and Monoclonal Immunoglobulins from Multiple Myeloma and Waldenströms, Macroglobulinemia May Express Similar Antibody Specificities," Ann. Immunol. (Ins. Pasteur) 132C:231–236 (1981).

Wyman et al., "A Highly Polymorphic Locus In Human DNA," Proc. Natl. Acad. Sci. USA 77:6754 (Nov. 1980).

METHODS OF IDENTIFICATION EMPLOYING ANTIBODY PROFILES

RELATED APPLICATIONS

This application is a continuation-in-part of Applicant's copending application Ser. No. 07/071,707, filed Jul. 9, 1987, now U.S. Pat. No. 4,880,750 entitled "Individual-Specific Antibody Identification Methods," which application is incorporated herein by this reference.

BACKGROUND

1. The Field of the Invention

The present invention is related to identification of individuals, and fluids and tissues obtained from individuals, through analysis of the antibodies carried by such individuals. More specifically, the present invention is related to the identification of individuals by analysis of the antibody profile of such individual. The present invention is further related to distinguishing one individual from another individual by comparing the antibody profiles of said individuals.

2. Technical Background

In various contexts it is very important to identify individuals with a high degree of accuracy. It is also important to have the capability to differentiate individuals, one from another. Furthermore, it is also important for some purposes to link tissue, body fluid, or other biological samples with the individual producing such samples.

The need for such identification methods may arise in any one of a wide variety of situations. For example, the need for accurate means of identification is obviously necessary in law enforcement. It may be critical in the investigation of a crime to link tissue, blood, semen, or the like, left at a crime scene with the owner of such biological material. If such material can be linked to a specific individual, law enforcement authorities will be aided immeasurably in solving the crime and apprehending and convicting the criminal.

Similarly, identification of individuals is important in determining paternity or maternity. Determination of parenthood arises in a number of contexts. For example, it may be important to identify mothers and newborns in the hospital setting in order to match the appropriate newborn with the appropriate mother. It may also be important to determine parenthood for purposes of immigration and naturalization. Many countries grant favorable immigration status to immediate family members of citizens. However, establishing a familial relationship may be difficult in some cases. In addition, the subject government has a related interest in preventing immigration fraud.

Various screening techniques are presently employed in order to determine parenthood. These include blood typing and comparing other physical characteristics. As will be discussed in more detail below, it is now possible to do some paternity screening by analyzing the DNA of the individuals involved. Each of the techniques used in the past, however, has serious limitations.

Another situation which calls for the matching of tissue or biological fluid samples with an individual is in the area of biological testing. Many types of biological tests are presently employed. These include urine tests, blood tests, and tests on tissue samples for cancer and other diseases.

In the context of such tests, there is a corresponding need to assure that the proper sample is attributed to the appropriate individual. If, for example, an individual is a drug user, it will clearly be to that individual's benefit not to be tied to a drug containing urine or blood sample. Examples of where this type of situation could arise include drug testing of athletes, drug testing of race horses, and employee drug testing of the type now carried on by numerous employers. In these contexts individuals have attempted to alter results, switch samples, or otherwise attempt to defeat the effectiveness of the test. If samples could be precisely matched to the individual, these problems could be minimized.

Similarly, it is important that samples used for diagnosis of disease be correlated to the donating individual in order to provide an accurate diagnosis. Again there are documented cases of samples being inadvertently switched, resulting in difficulty in providing accurate diagnosis of disease.

Other situations where if may be important to match, or even separate, biological materials would be in the context of a disaster or war zone where it is desirable to match body parts. In this type of context it may be difficult or impossible, using known techniques, to separate or match body parts with any degree of accuracy.

In order to accomplish sorting of biological samples, identification of individuals, and other related tests, various techniques are now used. The three most common non-visual means for identifying people include blood typing, fingerprinting, and voice exemplars. Other methods include retinal scans and dental x-rays.

Blood typing is based on the existence of groups of antigens present on blood cells. For example, the ABO system refers to four different groups of blood cell antigens: A, B, AB, and O. The letters designate antigens present on the surface of the red blood cells. Type A individuals have the A antigen; Type B individuals have the B antigen; Type AB individuals have both antigens; and Type O individuals have neither the A nor the B antigen.

By analyzing a sample of a person's blood it is possible to identify that individual to a particular blood group. It is, of course, immediately apparent that while this method may be used to identify an individual out of a small group of individuals, the method is limited when identification of an individual out of thousands is the goal. To do this, testing for many more blood group antigens is required and each test is a separate assay. Some newer tests make use of different isozymes that are present in body fluids, yet these tests also suffer from the same limitation as do the blood typing tests. These methods can exclude certain individuals, but they cannot typically differentiate among a large number of individuals, or between members of the same blood group.

Fingerprinting is perhaps a more accurate way of identifying an individual, and is widely used by virtually all law enforcement agencies around the world. It is based on the appearance of characteristic patterns of an individual's fingers, such as swirls, valleys and ridges. When this method is used, a statistical evaluation is given as to the degree of correspondence between known fingerprints obtained from the individual, and those fingerprints which are sought to be matched to the individual. The procedure is technically arduous, and often not definitive. For example, the way that fingerprints are catalogued allows room for ambiguities.

Furthermore, in many instances of crime, fingerprints are not available.

The third procedure for identifying individuals is to match a voice recording with a voice exemplar of the individual. It is, of course, apparent that this method has little value in most instances, as there is seldom access to a recording of an individual's voice prior to the time that the match is sought.

A variety of immunological/biochemical tests based on genetics, are routinely employed in paternity testing, as well as for determining the compatibility of donors and recipients involved in transplant or transfusion procedures, and also sometimes as an aid in the identification of human and animals. Generally, the existing procedures involve serological testing for proteins encoded by the Human Leukocyte Antigen gene loci or, as it is more commonly known, HLA complex.

Although a good deal of information is known concerning the genetic makeup of the HLA locus, there are many drawbacks using HLA serological typing as the means for identifying individuals in a large group. This is primarily because of the complexity of the serum used to do the testing, and the lack of widespread availability of standard serum necessary to conduct the test, especially when dealing with species other than mouse or man. Each of the HLA antigens must be tested for in a separate assay, and many such antigens must be identified in order to identify one individual, an arduous process when trying to identify one individual in a large group.

In addition to serological and mixed lymphocyte testing for the products of the HLA loci, more recent studies have identified DNA restriction fragment length polymorphisms (RFLP'S) indicative of different individuals, and these have been used in paternity testing, and transplant and transfusion compatibility testing. Other workers have developed identification systems based on the analysis of repetitive DNA sequences (called "hypervariable minisatellite" regions or "variable number tandem repeats" in human DNA. This method can also be applied to animals. The systems that are based on DNA RFLP, or DNA "hypervariable minisatellite" regions, however, do not discriminate between genetically identical animals such as twins, and depend on the particular DNA probe used to discriminate between individuals that are closely related.

It will be appreciated that while the above methods are useful for identifying individuals, performing paternity tests, and for transplant and transfusion compatibility testing, these methods are presently technically arduous when used for the purpose of identifying individuals. DNA and related testing methods are also time-consuming and often necessitate the use of expensive laboratory equipment.

Accordingly, it would be a significant advancement in the art to provide a single test for determining identity, separating individuals, and for determining the source of biological fluids and tissues. It would be further advancement in the art if such a test could be provided which was sufficiently powerful to identify individuals with a very high degree of certainty. It would also be a significant advancement in the art to provide such a test which was much more simple to use than many known tests (such those employing DNA analysis). It would be a further advancement in the art to provide kits for use and employment of such a test method.

Such methods and apparatus are disclosed and claimed herein.

BRIEF SUMMARY AND OBJECTS OF THE INVENTION

The present invention presents a general identification method whereby individuals, and tissue and body fluid samples associated with those individuals, can be identified. The invention is based upon the discovery that humans and other animals carry an individual set of autoantibodies and, therefore, have a unique individual antibody profile. That is, the specific antibody makeup of each individual is unique in much that same way that each fingerprint is unique. The combination of antibodies and the specific characteristics of those antibodies is unique for each individual.

Much like fingerprint development, the individual antibody profile (also sometimes referred to as "antibody fingerprint" or "individual specific antibodies") is the unique product of the normal developmental process. The immune system of each individual is highly variable when producing antibodies in response to antigens. In addition, the antibody genes are known to undergo a high degree of somatic mutation, acting effectively as a random number generator. These factors lead to further diversity of the antibody repertoire.

The present invention shares with DNA fingerprinting the ability to discriminate between closely related individuals. It has the additional advantage, however, of being able to discriminate between identical twins. As will be discussed in additional detail below, the method is very simple and does not require extensive training and expensive equipment in order to conduct tests using the method.

The method provides a simple immunological identification method that is applicable to humans and animals generally. The method is premised on the generation of an antibody mediated immune response. Any tissue or body fluid sample having an effective quantity of antibodies can be used. This results in the formation of antibody-antigen complexes which are highly distinctive of the donor organism. All individual specific antibody isotypes are represented, thus allowing for the use of a wide range of detector molecules. The detector molecules used to detect the antigen-antibody complexes are widely available and include antibody binding proteins such as Staphylococcus aureus Protein A, or antibodies such as goat anti-human antibody or rheumatoid factor, or even cells with receptors for antibodies, such as lymphocytes.

The detector molecules are appropriately labeled with tracer molecules; examples of such being enzymes, radioactive isotopes, magnetizable metals, or photosensitive chemicals. The signals generated by the detector molecules on binding to the antigen-antibody complexes are then analyzed visually, or with appropriate instruments such as optical scanners or gamma radiation scanners. The profiles can be computer analyzed and stored for comparison at a later date with profiles from samples of known origin.

In addition to presenting a method for identifying people and animals, the present invention also provides a method whereby severed body parts from people or animals can be identified. This situation might arise, for example, as a result of a catastrophic event such as an airplane crash, automobile crash, or war zone, where bodily parts may be identified using antibody profiles.

The present invention also presents an embodiment of the antibody fingerprint method termed the blocked fingerprint assay. The method relies on competition by an effective concentration of antibody for epitopes present in a panel of multiple or primary antigens, with similar epitopes present in other antigenic or secondary molecules, usually in solution. This leads to inhibition or blocking of the formation of the antigen-antibody complexes on the panel on which is formed the antibody fingerprint. Thus, the number of elements in the fingerprint is reduced.

The blocking assay can be used, in a single assay, to detect many different secondary antigenic molecules with the same epitopes as are present on the primary antigens in the panel such as allergens, autoantigens, or environmental antigens such as infectious agents, chemicals, toxins, or synthetic peptides, as appropriate. This method also allows the identification of an individual's antibodies with antipathogen, anti-allergen, or autoantibody function. The antibodies thusly identified are useful in their own right in the construction of diagnostics for pathogens or allergens, therapeutics or diagnostics for autoimmune diseases.

The present invention also provides kits that can be used to identify animals or security documents that consist of individual specific antibodies and accompanying reagents.

DETAILED DESCRIPTION OF THE PREFERRED EMBODIMENTS

Figure 1:
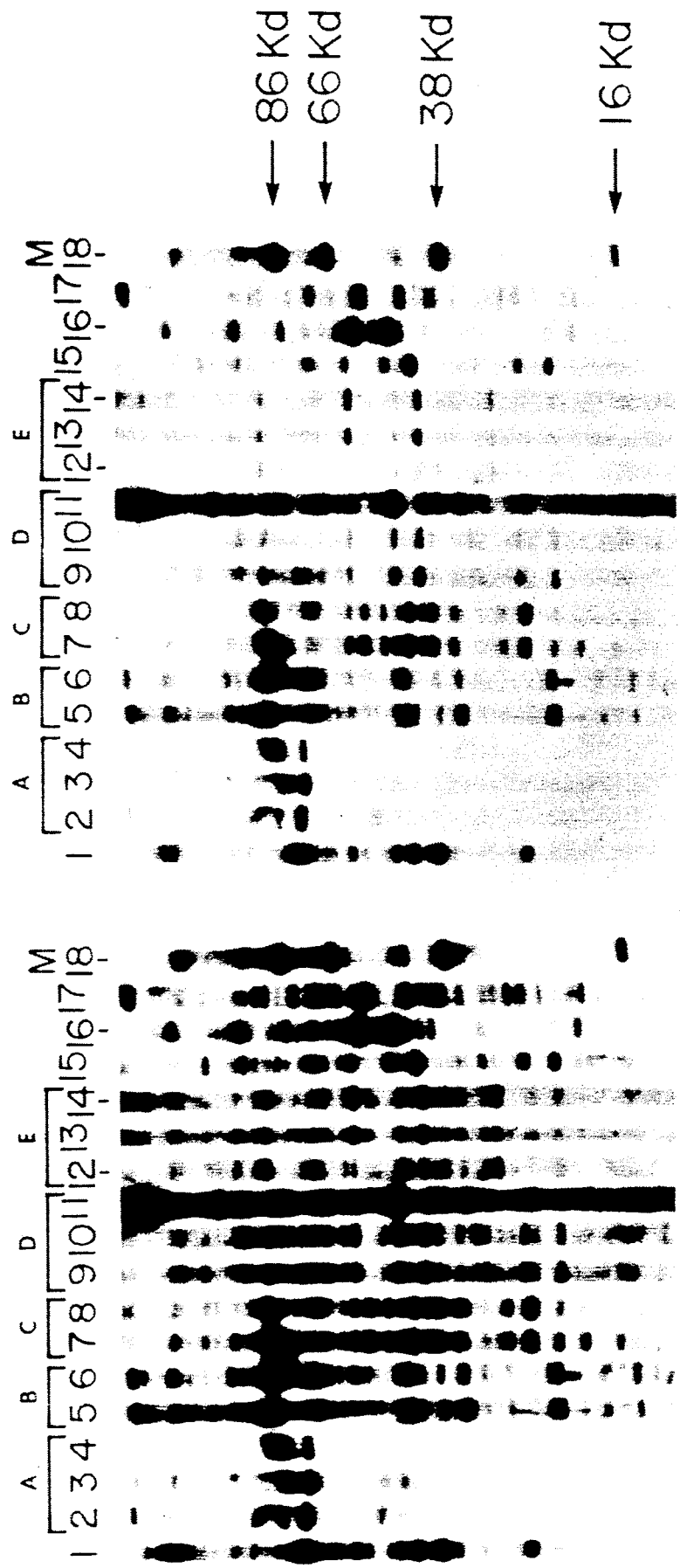
FIG. 1 shows the instant invention or antibody profiles obtained with individual human sera, including members of two families, over a period of years, and in one instance, when gravely ill. The sera were screened against a panel consisting of some ten thousand different human (HeLa cell) antigens and the antigen-antibody complexes were detected with 125 I-labeled S. aureus Protein A that exposed Kodak X-AR film.

The present invention is related to the use of an individual's unique set of antibodies (sometimes referred to as "individual specific antibodies," "antibody profile," or "antibody fingerprint") to identify that individual, or to distinguish individuals from one another. The present invention is also useful in simply sorting tissue or fluid samples, even though the results of the test are not compared with any specific known.

The present invention provides a generally applicable identification method that is rapid and simple. It is premised on the finding that animals with an immune system react to the presence of foreign substances, or antigens, by mounting an immune response which involves the production of antibody molecules by lymphocyte cells. The antibody response is maintained over a multi-year period. During the early development (aged newborn to two years old in the case of humans) of each individual's immune system, an effective individual-specific antibody response is obtained, involving a large number of different antibody molecules.

Consequently, individual-specific antibodies present in the body fluids or solids of humans, or animals, can act effectively as an individual-specific "fingerprint" of that individual when screened against a suitable panel (n dimension array where n is usually one or two) containing multiple antigens. The effective number of antigens or epitopes (antibody-binding sites) that are present in the antigenic array is less than $10^{20}$ and typically greater than one thousand, depending on the level of statistical certainly desired in matching or discriminating between a few or a large number (greater than 100) of individual antibody "fingerprints." The antigen-antibody reactivity profile, when detected with an appropriate detector molecule, provides a specific antibody profile for each individual.

The identification method of the present invention can be used to identify humans, or any organism that produces a unique individual set of antibodies. Moreover, the method can be applied to distinguishing between or identifying inanimate objects such as blood transfusions, body parts, body excretions, biological samples providing drug or diagnostic test results, or security documents containing such antibodies. Further, it will be appreciated by those skilled in the art that elements of the antibody profile may reveal much useful information about the immune status of an individual.

A unique feature of the present invention is that it is sensitive to persistent environmental antigens. In the blocked fingerprint assay, one embodiment of the instant method described below, the ability of secondary antigens is described such as environmental antigens, that compete with an effective amount of primary antigens in the panel for limited individual-specific antibodies. Successful competition leads to a loss of antigen-antibody reactions with primary antigens in the panel, and subsequent loss of elements of the antibody fingerprint. Antibodies that effectively cross-react with primary antigens in the panel, and with different secondary antigens can be used to identify immunologically similar allergens, infectious agents, chemicals and toxins.

The blocked fingerprint assay can also be used to detect persistent antigens that are natural or synthetic "autoantigens" that possess similar epitopes as do the primary antigens in the panel (autoantigens are defined as "self" antigens). Conversely, when the primary antigens in the panel consist of "self" or "autoantigens," or pathogens, the blocked fingerprint assay can be used to identify environmental antigens with similar epitopes as the autoantigens or pathogens, respectively. Some individual-specific antibodies probably correspond to "autoantibodies" and on purification, may be useful in and of themselves, in the construction of diagnostics and therapeutics for autoimmune diseases.

Similarly, if the primary antigens correspond to pathogens in the environment, then the blocked fingerprint assay can be used to identify individual-specific antibodies with antipathogen function. These individual-specific antibodies may also be used in the construction of anti-pathogen diagnostics or therapeutics, such as vaccines. Thus it is readily apparent that this application of the method described herein has applications in the area of diagnostics and therapeutics for autoimmune diseases of man and animals.

The immunological method also may be used in conjunction with other identification methods based on different principles, such as traditional fingerprinting, genetic tests such as HLA testing, DNA RFLP assays, or DNA fingerprint assays. The several tests taken together can be expected to provide a particularly accurate and powerful identification method, especially in situations involving a large number of individuals. The present method has advantages of rapidity, simplicity, and cost effectiveness, especially when easily obtainable fluids are used, thus avoiding the problems of blood letting.

The basic immunological method, as applied to the identification of individuals includes:

(a) Obtaining an effective concentration of antibodies from an individual's body fluid or tissue. The antibodies may be obtained in the dry state and as in the case of body solids, resuspended into solution using a suitable buffer, such as isotonic saline. The effective concentration of each antibody specificity is less than 1 g/ml, preferably about 10 ng/ml–10 mg/ml.

(b) Reacting the antibody solution obtained in (a) with an effective panel of antigens where panel refers to an n-dimensional array of antigens, where n is typically one or two, to form antigen-antibody complexes. The panel of antigens contains multiple different antigens, typically, but not necessarily, greater than ten thousand different antigens or epitopes. The array may be composed of natural antigens prepared from tissue cultured cells, or may consist of such extracts treated with enzymes or in other ways to generate fusion proteins or degradation fragments of different size. Alternatively, the array may consist of purely synthetic polypeptides, or may consist of mixtures or subfractions of any of the above, so long as the antigens in the panel contain epitopes recognized by the individual-specific set of antibodies being tested, and so long as the antigens are not contaminated with antibodies.

The number of antigen-antibody complexes may be effectively increased or decreased by mixing the different kinds of antigens used in the panel. The effective concentration of each antigen in the panel is less than 1 g/mm$^2$, and preferably 0.5 nanogram to 1 mg per square millimeter. The panel of antigens may be formed by separating the antigens in n dimensions which is typically one or two, and can be effected by electrophoresis, isoelectric focusing, or other means.

(c) Detecting the antigen-antibody complexes with an effective amount of an appropriate detector molecule.

The identity of an individual is established by comparing the resulting antigen-antibody reactivity profile, or antibody fingerprint, with that of an earlier obtained profile known to be characteristic of the individual. Similarly, individuals or inanimate objects, such as blood transfusions or tissues obtained after an air crash, may be distinguished by comparing antibody fingerprints obtained from each. In addition, samples may simply be sorted, thus avoiding the necessity of comparing the results with a known. For example, two blood sample may be tested to determine whether or not they originated with the same individual.

A wide variety of assay techniques are available for detecting antigen-antibody complexes, commonly referred to as "immune complexes." It will be appreciated by those skilled in the art that the instant invention does not rely on an understanding of the molecular interaction of each particular antibody and antigen. All that is necessary is that a method be employed for detecting the immune complexes formed as a result of the individual's antibodies reacting with multiple antigens present in a panel or array.

A variety of immune complex assays are known and described in the art. One type of assay is termed analyte excess/labeled antigen assays. Although these assays can be applied to realize the instant invention, they are tedious and time-consuming in that they are generally used to determine the presence of a single antigen. Since the instant method relies on a determination of the reactivity profile of multiple antibodies with multiple antigens, it will be appreciated that to obtain this information using analyte excess/labeled antigen assays would require considerable time, wherein multiple different assays are performed for each antigen.

The second broad class of immune complex assays can be considered antigen/labeled antibody excess assays. Here, the antibody composition of normal sera is accelerated by screening the sera against a mixture of antigens generally bound to, and separated on, a solid surface. The antibody present in sera is in excess, and hence the phrase "excess antibody assay." The antigen mixture can be attached to a wide variety of solid surfaces, and then assayed by applying the sera. A second labeled antibody or antibody-binding molecule is applied which reveals the presence of antibody bound to the antigen present in the sera.

Typically, the antigenic material is separated in some way, most often by electrophoresis, to allow ready visualization of the reactivity profile of antibodies in the sera with multiple antigens. A wide variety of materials have been used to construct solid support matrices that can be employed in these types of immune complex assays. Representative materials include polyacrylamide and agarose. In addition, other materials including polystyrene, polyvinylchloride, polyethylene, cellulose, and other natural or synthetic polymers may be employed.

A modification of the above-mentioned technique is the so-called immunoblotting procedure, also called Western blotting, described by Towbin et al. in Proceedings of the National Academy of Science, USA, Volume 76, page 4350 (1979). This consists of separating an antigen mixture in one or two dimensions on a polyacrylamide gel, and then transferring the antigens from the gels onto a suitable surface, for example, nitrocellulose paper. The procedure generates a panel of antigens arrayed in one or two dimensions. The panel of antigens is then incubated with a blocking agent, for example a solution of bovine serum albumin and detergents, such as Tween-20, to block or bind to sites on the panel that are not occupied by antigen.

The panel is subsequently incubated with primary antibodies, washed to remove non-specifically bound antibodies, and then incubated with a detector molecule that recognizes the antigen-antibody complexes, typically through the antibody portion. The immunoblotting technique is advantageous in that it generally has lower background than other techniques, and further, it lends itself to a dipstick assay. The instant method is different from those previously described for the formation or detection of immune complexes because it involves individual-specific antibodies.

The method of detecting antibody bound to antigen using a tracer-labeled antibody-binding molecule will differ depending on the nature of the substrate material to which the antigen is attached, the nature of the antigens themselves, and the nature of the antibodies involved. Traditional methods utilize *S. aureus* Protein A or a labeled second antibody directed against the first antibody, wherein the label is most often radioactive, or an enzyme capable of hydrolyzing a substrate thereby producing detectable color. The color can be associated with fluid surrounding the matrix, or can be associated with the matrix itself.

It will be appreciated by those versed in the art, that the second antibody itself will give an antibody fingerprint in the instant method, and is first preferably incubated extensively with the panel of antigens to adsorb out second antibody-specific individual-specific antibodies present. The adsorbed second antibody may then be used as a detector molecule when combined with a suitable reporter molecule well known to those skilled in the art. By adsorbing the second antibody to remove individual-specific antibodies present, clear antibody fingerprint profiles are realized. Immunoblotting enables antibody binding to antigen to be detected by visualizing colored particulate precipitates and avoids the use of radioactive compounds. An effective concentration of antibodies present in immune complexes is typically 1 ng to 10 ug per complex per $mm^2$.

A number of enzymes can be coupled to protein A or second antibody, that form precipitates on a solid surface in the presence of a suitable substrate. A partial list includes horseradish peroxidase, glucose oxidase, and alkaline phosphatase.

In addition to enzymatically revealing the antigen-antibody complexes formed on a solid matrix, there exist non-enzymatic means of revealing the immuno complex. Many of these are well known to those skilled in the art, but perhaps particularly useful is the colloidal gold technique. The manner in which it is constructed and used with antibodies is described by De Mey et al. in *Prot. Biol Fluids* (Editor Pepters), Paragon Press, Oxford, page 943 (1981), and Ami in *Immunochemistry: Applications and Pathology and Biology* (Editor Polak and Van Noorden) and Wright and Sons Ltd., London, page 83 (1983).

A preferred embodiment of the instant invention involves constructing a panel of one to ten thousand different antigens, using the immunoblotting procedure described by Towbin et al. Proceedings of the National Academy of Sciences, Volume 76, page 4350 (1979). The particular antigens used in the panel may vary, depending on the number of antigen-antibody reactions desired. For example, human HeLa cells contain approximately ten thousand different antigens, and can be prepared and separated electrophoretically according to molecular mass, using denaturing polyacrylamide gel electrophoresis systems, and subsequently electrophoretically transferred onto a matrix, such as nylon or nitrocellulose paper. The antigens are prepared according to appropriate protocols, for example, see Francoeur et al., Journal of Immunology, Volume 136, page 1648 (1986).

Unlike previously documented use of the immunoblotting technology, the instant invention is based on the formation and detection of immune complexes formed with individual-specific antibodies. A different individual-specific antibody fingerprint or profile is obtained if a single individual's antibodies are reacted with total HeLa cell antigens, or partially degraded HeLa cell antigens. In both cases, the antibodies are likely the same, but the HeLa antigens are different in molecular mass and size. Thus, the antigens are located in different areas of the panel.

An effective quantity of antibodies is obtained from an individual's body fluids or solids, and reacted with the panel of antigens for a time sufficient for the antibodies to bind antigen, typically for 30 minutes to an hour, but not more than three days. The antibodies are incubated neat (undiluted) or in an appropriate solution (e.g., isotonic saline) at a dilution of about less than one in $10^7$, preferably in the range of 1:10 or 1:20. The effective concentration of each antigen in the panel is less than 1 $g/mm^2$, preferably 0.5 nanogram to 1 mg per square millimeter.

The nonspecifically bound antibodies are removed by washing, and the immune complexes detected by further incubation with an effective concentration of a labeled detector molecule such as $^{125}$I-Protein A, or with a labeled second antibody such as alkaline phosphatase-conjugated goat anti-human IgG, previously adsorbed to remove second antibody-specific antibodies reactive with the panel of antigens. The panel of antigens is washed to remove nonspecifically bound detector molecules, and an effective concentration of substrate material added if the second antibody carries an enzyme, resulting in the development of a colored product. If the detector molecule carries a radioactive tracer, X-ray film or other techniques can be used to detect the presence of the detector molecules by methods well known to those skilled in the art.

The antibodies present in particular individual sera or other body fluids or solids, can be employed to identify or distinguish between inanimate objects, such as blood or body parts, or security documents. For the latter, a particular panel of antigens can be employed for this purpose as well, to be used to generate an antibody fingerprint with a particular individual's antibodies.

The present invention is also related to a kit for use in performing the method of the invention. The kit may take any one of a variety of forms. In one embodiment, the kit comprises a panel of multiple antigens as described herein. In one embodiment, that panel consists of a panel of HeLa cell antigens separated in n dimensions, where n is one or two. For some applications there may be more than one type of strip of antigens. For example, there may be one type of strip with HeLa cell antigens, and another with antigens from another cell line or other source.

The kit also includes an effective quantity of detector material. The detector molecule is of the type described herein, and may produce a pattern detectable by radioactive methods, colorimetric methods, or any other method that allows the pattern of antibodies to be detected.

The detector can either directly label the individual-specific antibodies in the sample, or the molecule may bind (adsorb) to the antibodies in the user's samples. There may be only one type of molecule, or there may be a series of two or three molecules that are used sequentially during the course of the assay. One of these, typically the last one in the sequence, will be coupled to a molecule that will allow the visualization of the antigen-antibody-detection molecule complex. This may be a radioactive molecule, an enzyme that will allow colorimetric or other detection, or even a colored reagent directly coupled to the detection molecule.

When the detection system involves an enzyme, a substrate for the enzyme is used to visualize its presence. In one preferred embodiment of the invention, the visualization is colorimetric, however, it could also be chemiluminescent, and may use yet to be developed substrate materials.

It will be appreciated that the kit may include a wide variety of related supplies. For example, it may be preferable to include items such as trays for incubating samples, squirt bottles for wash solution, and disposable pipets for measuring.

For some bodily fluids, the individual-specific antibodies may need to be extracted from the fluid before they can bind to a strip. Kits designed for use with these fluids will include the reagents necessary to prepare the sample for use.

Typically the kit will be used to test samples provided by the user. Such samples may originate from a crime scene or they may constitute two samples and the question may be whether they both contain a small sample of individual-specific antibodies to be used as a positive control in the assay. An exception to this situation is in conjunction with the blocked fingerprint assay described above. In that situation, the kit may contain a standard set of individual-specific antibodies, and the user would supply the sample to be tested.

In using the kit, the user must only follow a simple protocol in most situations. This protocol is as follows: (1) dilute the samples to be tested and incubate them with the strips of antigen; (2) wash the strips as described herein; (3) incubate the strips with the detection molecule; (4) wash the strips; (5) repeat steps 3 and 4 if there is more than one step in the addition of detection molecules (in one embodiment there are two steps, namely an incubation with protein A-biotin, followed by an incubation with streptavidin-alkaline phosphatase); and (6) in the case of enzymatic detection system, incubate the strips with the substrate.

EXAMPLES

The following examples illustrate various aspects of the invention, but it will be obvious that various changes and modifications may be made therein without departing from the scope of the invention. For example, total antibodies, including the individual-specific antibodies, from a particular individual may be labeled directly by reaction with detector molecules, and the detector antibody complexes subsequently incubated with the panel of antigens, thus generating an antibody fingerprint. Another example, perhaps more properly called an antigen fingerprint, includes first separating the total antibodies (e.g., by isoelectric focusing), and then reacting the antibodies with a mixture of labeled or unlabeled antigens, or a particular antigen detector molecule. The immune complexes formed are detected directly, or after reaction with a labeled detector molecule.

EXAMPLE I

'Antibody Fingerprinting' of Humans

An extract of human HeLa cells was prepared and used to form an antigenic panel as described in Francoeur et al., Journal of Immunology, Volume 136, page 1648 (1986). HeLa cells were grown in standard laboratory tissue culture medium, isolated, lysed with a detergent, and centrifuged to remove any insoluble debris. The extract contained approximately ten thousand immunogenically different antigens, the bulk of which have not yet been antigenically defined. The material was subjected to electrophoresis on a sodium dodecyl sulfate polyacrylamide gel to separate the mixture according to molecular mass. The separated antigens present in the polyacrylamide gel were electrophoretically transferred onto Immobilon paper (obtained from Millipore Corporation) and the sites on the paper with no antigens bound were then blocked by incubation with a solution containing 4% instant powdered dry milk, using standard techniques. The paper was cut into strips approximately two millimeters in width. Each strip consists of a panel of some ten thousand different antigens arrayed in one dimension according to molecular mass.

Separate panels of antigens were incubated with individual sera (containing individual-specific antibodies), diluted 1:20 in the appropriate buffer, obtained from different individuals at different times, in this case, for three hours at room temperature, with constant agitation. The panels of antigens were washed, to remove unbound or nonspecifically bound antibodies, and incubated with $^{125}$I-Protein A for two hours. Following subsequent washing to remove unbound detector, the panels of antigens were dried and exposed to X-ray film for 4 hours at $-70°$ C. with an enhancer screen, and the film developed, according to established protocols.

FIG. 1 shows two different exposures of the film; a long (3-day) and short (8-hour) exposure. The fingerprints are stable over a period of 4 years, 2 months for one individual (lanes 2–4); for 6 years, 7 months for a second individual (lanes 5 and 6); for 7 years for a third individual (lanes 7 and 8); for 7 years, 4 months for a fourth individual (lanes 9–11), and for 8 years, 3 months for a fifth individual (lanes 12–14). identical at early and late times, and are constant over a multiyear period. The individual whose fingerprints are shown in lanes 9 and 10 became gravely ill (vasculitis), and his fingerprint is obtained during this condition (lane 11). It is apparent that during the illness, the amount of antibody-antigen complexes was increased and thus the intensity of the fingerprint was stronger than when he was well. Minor changes in the fingerprint were detected.

The second individual (lanes 5 and 6) is the daughter of the third individual (lanes 7 and 8). While the fingerprint of the mother and daughter are unique to those individuals, certain elements within the fingerprint appear to be common to both, suggesting that they share a common environment and/or genetic background that influences the immune response similarly.

The fourth individual (lanes 9–11), is the son of the first individual (lanes 12–14), and again, while the fingerprints of the son and mother are unique to each individual, certain elements within the fingerprints are common to both. Lastly, lanes 1 and 15-17 show fingerprints of unrelated individuals while lane 18 shows the control fingerprint used for quality control. The molecular mass (Mr) of the antigens used in the panel is shown in kilodaltons (Kd).

EXAMPLE II

Figure 2:
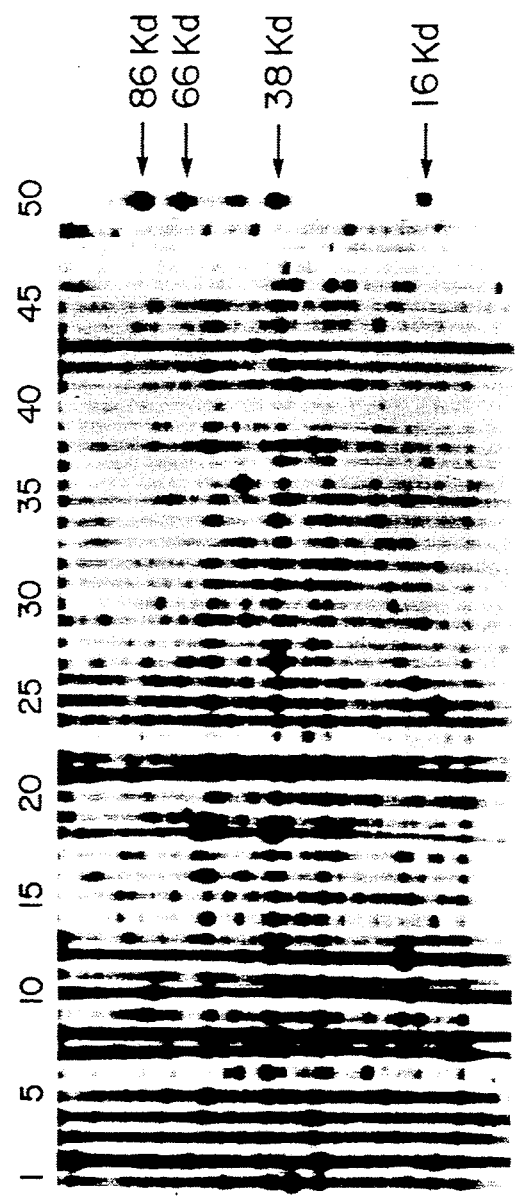
FIG. 2 shows the antibody profiles of individual normal humans ranging in age from newborn to ninety years old, using a HeLa cell panel of antigens.

Antibody-antigen Reactivity Profiles, or Antibody Fingerprints of Old and Young Normal Humans The method of the instant invention is applicable to both young and old humans. FIG. 2 shows the antibody fingerprints obtained from sera of normal individuals aged newborn to 90 years old. The panel of antigens and detector molecules used were the same as described in Example I. Approximately equal numbers of males and females are represented. An individual-specific profile was obtained in all cases. Some or all of the individual-specific antibodies in newborns are likely transferred from the mother to the fetus of maternal antibodies in general are known to be passed to the fetus via the placenta, and are replaced by the child's own antibodies by approximately the sixth month after birth. The individual-specific antibodies appear to be fixed by approximately two years of age (see also Examples IV and V). Lanes 1-7, 80-90 years; lane 8, 20 years; lanes 9-18, 70-79 years; lanes 19-28, 60-69 years; lanes 29-38, 50-59 years; lanes 39-42, 40-49 years; lanes 43-45, 30-39 years; lanes 46-49, newborns. Lane 50 is a quality control fingerprint. The molecular mass (Mr) of the antigens in the panel is indicated.

EXAMPLE III

Antibody Fingerprints of a Single Normal Human Serum Obtained by Screening Against Different Panels of Antigens Norman human sera, or other body fluids containing antibodies, or similar fluids from other animals, can be screened against different panels of antigens prepared from complex antigenic mixtures.

Figure 3:
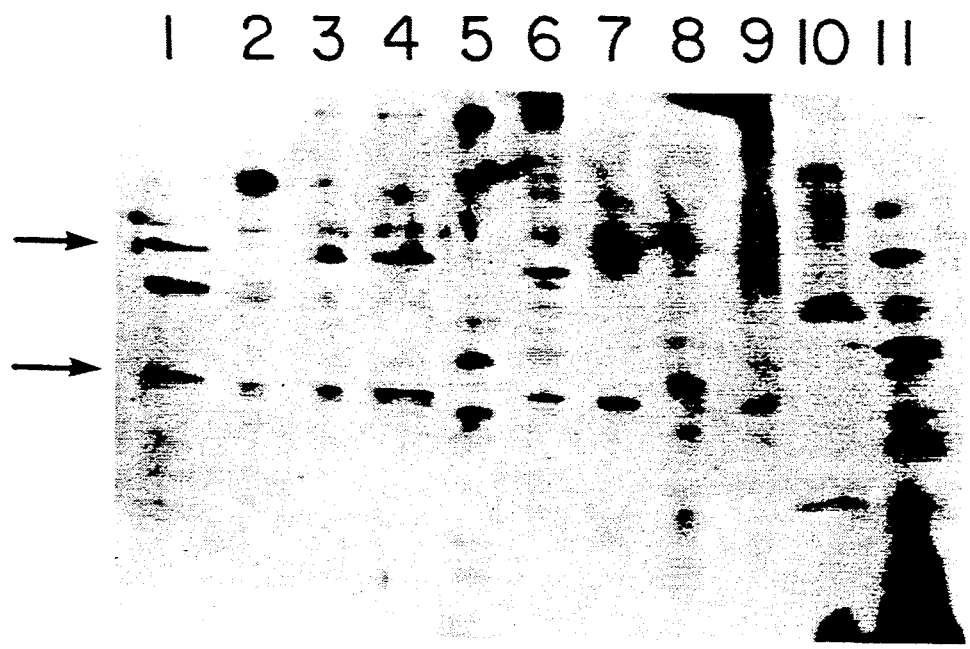
FIG. 3 shows antibody profiles obtained with an individual normal human serum screened against different panels containing multiple antigens prepared from various sources.

FIG. 3 presents antibody fingerprints obtained with a single normal human serum and reacted against panels of antigens prepared from human HeLa cells, a line of human cervical carcinomal cells that grow in the laboratory (lane 1); WIL-2 cells, a line of human B lymphocytes (lane 2); CV-1 monkey cells (lane 3); MDBK-cow cells (lane 4); dog muscle cells (lane 5); chicken embryo cells (lane 6); a mixture of different mouse cells lines (lane 7); frog oocytes (lane 8); Drosophila cells (lane 9); Bakers yeast (lane 10); RY1090 bacteria (lane 11). The detector molecule used was $^{125}$I-Protein A.

It is apparent that the sera yield different fingerprints with each antigenic panel tested. It is important to point out this finding permits a large number of antigens to be employed, and, moreover, permits a cross check of the identity of the individual.

EXAMPLE IV

Antibody Fingerprints of Various Children, Aged Two Days to One Year

Figure 4:
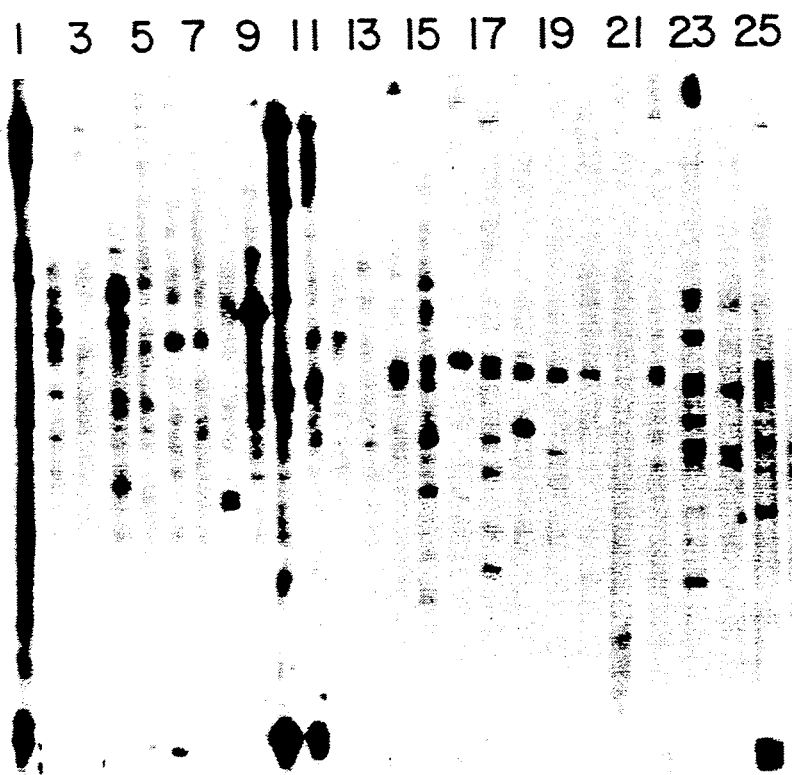
FIG. 4 shows the antibody profiles of individual normal and ill children aged one month to one year.

Sera were obtained from various male or female children, both normal and ill. The panel of antigens and detector molecule used were as described in Example I. The results are shown in FIG. 4. Lanes 1-26; female, 12 months, normal; male, 10 days, normal; female, 12 months, ill; female, 8 months, ill; female, 7 months, ill; female, 1 month, normal; female, lo months, normal: male, 12 months, normal: male, 4 months old, ill; male, 11 months, ill; male, 9 months, ill; male, 10 months, ill; male, 3 months, ill; female, 2 months, normal; male, 9 months, normal; female, 2 days, normal; female, 5 months, ill; male, 11 months, ill; male, 3 months, normal; male, month, ill; male, 2 days, normal; male, month, normal; female, 4 months, ill; male, 5 months, ill; male, 9 months, ill; female, 2 months, normal.

It can be seen that the fingerprints of children less than a year old are generally simpler than older individuals, presumably because the immune system is in its early developing stages, and the full complement of individual-specific antibodies is not yet established.

EXAMPLE V

Antibody Fingerprints of Various Children, Aged One Year to Six Years Old

Figure 5:
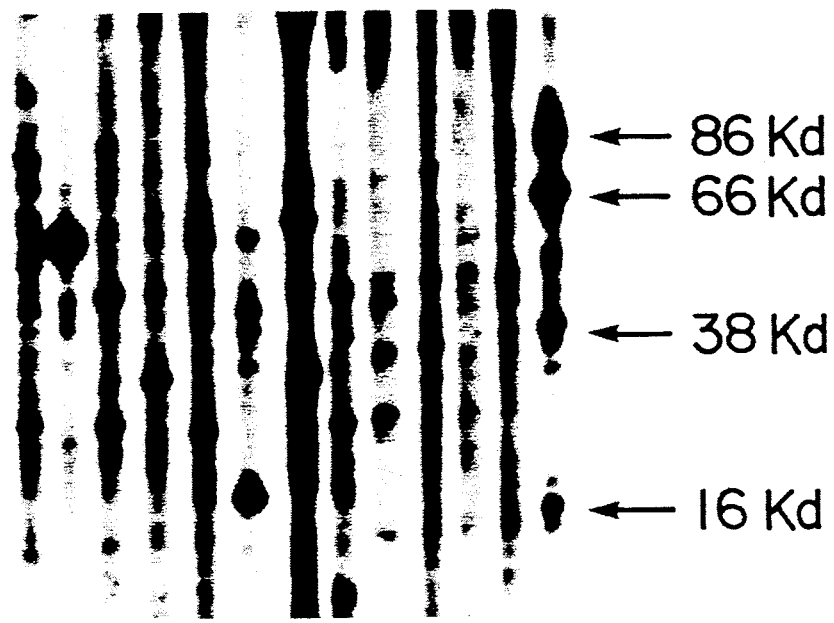
FIG. 5 shows the antibody profiles of individual normal and ill children aged one year to six years.

FIG. 5 shows that both normal and ill children of ages one to six years have an individual-specific set of antibodies that can be used to generate antibody fingerprints, similar to those of older individuals. The panel of antigens and detector molecules were as described in Example I. Lanes 1-12; female, 3 years, ill; male, 1 year, normal; male, 2 years, ill; male, 4 years, ill; female, 5 years, ill; female, 6 years, ill; female, 2 years, ill; male, 2 years, ill; female, 5 years, ill; male, 3 years, ill; female, 5 years, ill; male, 3 years, ill; male, 1 well; male, 1 year, ill. While it is clear from Example I that the antibody fingerprints are stable over a multiyear period, there is some indication that the fingerprints are altered by disease. The correlation with disease has been found so far is that in some instances there is an increase in the amount of total antibody which presents a more intense fingerprint (see FIG. 1, lane 11, FIG. 5, lane 7). Lane 13, quality control fingerprint. The molecular mass of the antigens in the panel is indicated in kilodaltons.

EXAMPLE VI

Antibody Fingerprints of Animals

Figure 6:
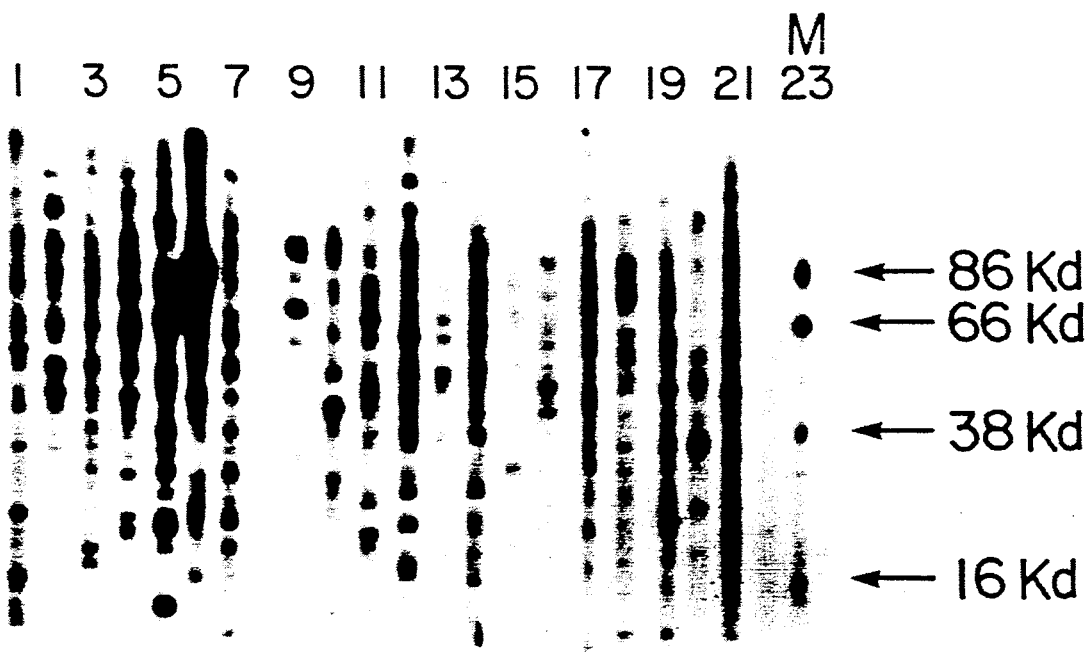
FIG. 6 shows the antibody profiles of individual normal and sick animals of different species and of different ages.

FIG. 6 shows antibody fingerprints of different animals. Sera was obtained from animals and tested against a panel of HeLa cell antigens. The detector molecule and antigens were as described in Example I. Lanes 1-3, 6, 15, 16, 19, 20, are sera from individual cats; lanes 4, 5, 7, 10-14, 17, 18, 21, are sera from individual dogs; lanes 8 and 9 are sear from individual monkeys; lane 22 is a horse serum; lane 23 is a quality control fingerprint. The various animals ranged from 2 months old to 18 years old and were approximately equally represented by both sexes. Most of the animals were well or had mild conditions, except for the cat and dog shown in lanes 5 and 6, which were gravely ill. FIG. 6 shows that antibody fingerprints may be obtained from different animals as well as from humans. The molecular mass (Mr) of the antigens in the panel is indicated in kilodaltons (Kd).

EXAMPLE VII

Antibody Fingerprints of Normal Human Families

Figure 7:
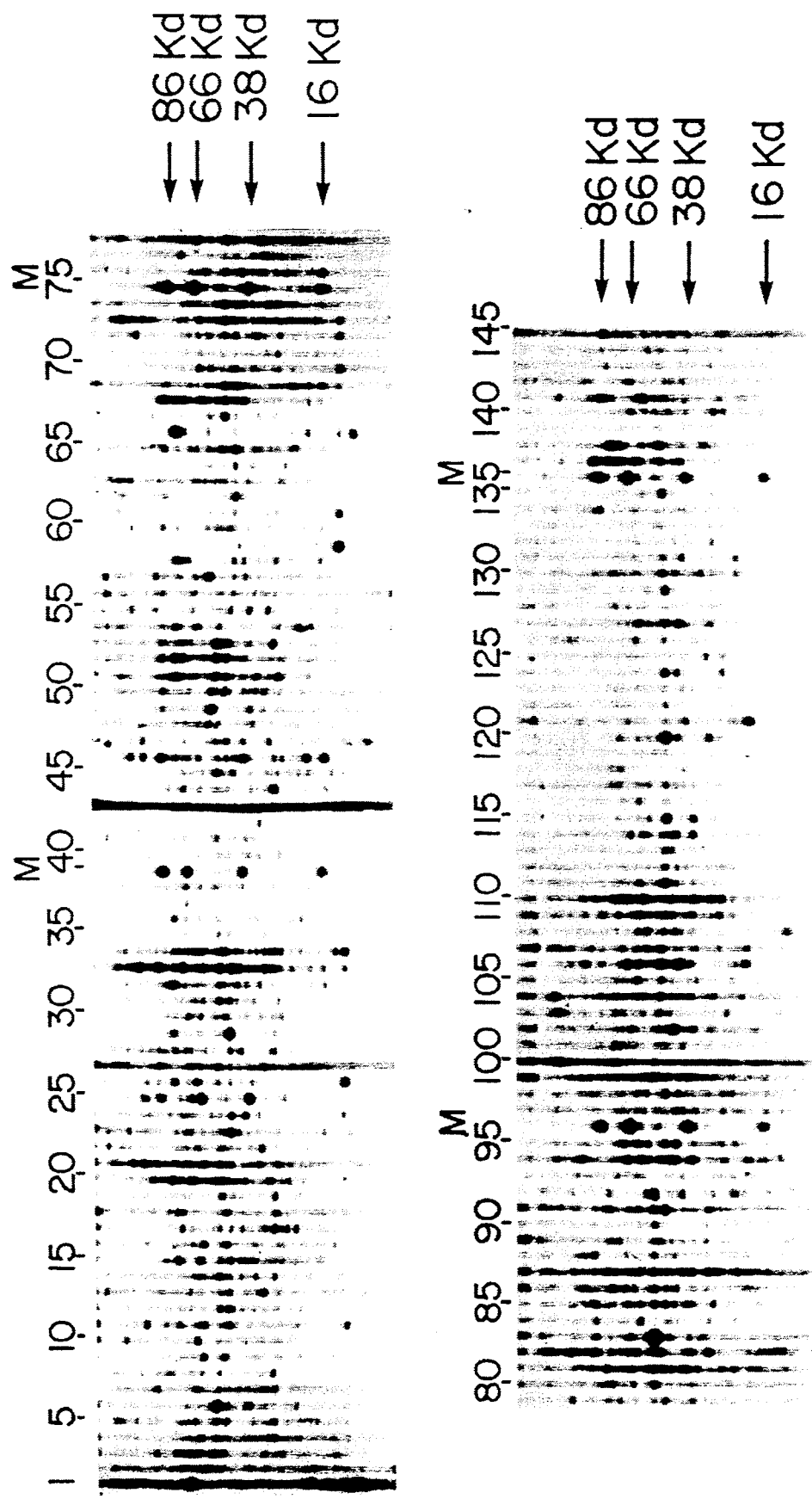
FIG. 7 shows the antibody profiles of individuals comprising different normal human families.

FIG. 7 shows antibody fingerprints of several normal human families. The children were all aged 12 years or older. The panel of antigens and detector molecules used were described as described in Example I. Despite the genetic relatedness of the individuals in the families, each individual has a unique antibody fingerprint. In some cases, common "motifs" within the fingerprints can be discerned, which appear to be shared by members of a family, suggesting a common response to common environmental antigens. Quality control fingerprints are designated "M." The molecular mass of the antigens in the panel is indicated in kilodaltons.

EXAMPLE VIII

Figure 8:
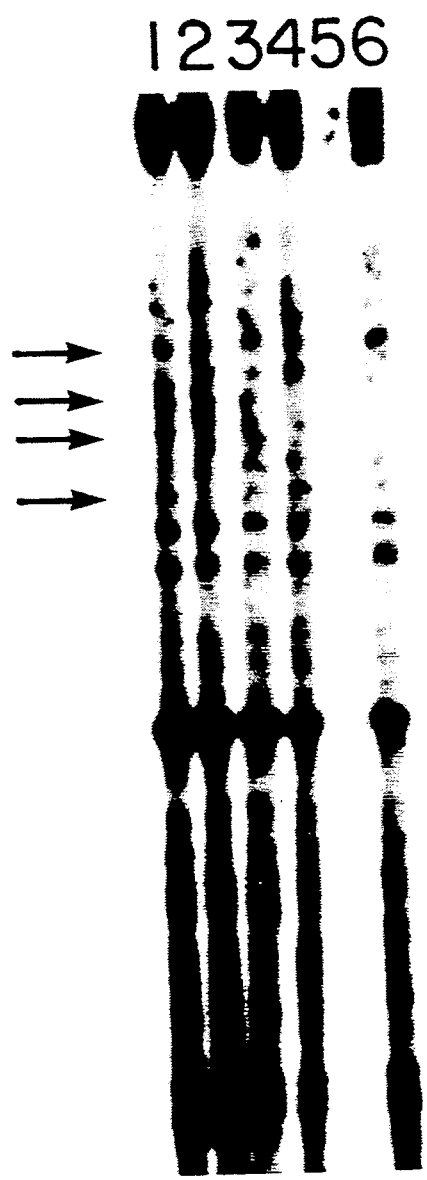
FIG. 8 shows the blocked fingerprint assay with secondary antigens in solution (obtained from different sources) used to compete with a panel of human HeLa cell primary antigens for IS antibodies present in an individual normal human serum.

The Blocked Fingerprint Assay as Used to Detect Environmental Antigens that Can Compete with Antigens in the Panel for IS Antibody Binding FIG. 8 shows the antibody fingerprints of a normal human individual, with or without the presence of competing secondary antigens The X-ray film was purposely overexposed to show the fine details of the fingerprints. The panel of antigens consisted of separated human HeLa cell antigens, and the detector molecule was $^{125}$I-Protein A, as described in Example I. Different mixtures of antigens were incubated simultaneously with the antibodies and the panel of antigens at the same time for two hours. All fingerprints should be identical if no blocking occurs.

Lane 1 shows the control lane, with no blocking agent. Lane 2 shows the results when human HeLa cell extract is used as the blocking agent. Two elements of the fingerprint are blocked arrows, bands 3 and 4), suggesting that one or more antigens present in the HeLa cell extract compete effectively with two HeLa antigens present in the panel for limiting individual-specific antibodies; lanes 3 and 6 show the effect of blocking with bacterial extracts. Three elements of the fingerprint are blocked each instance (bands 2, 3 and 4). Lane 4 shows the results when yeast extract is used as the blocking agent. One element of the fingerprint is blocked (band 3). Lane 5 presents a control for the detector molecule in which the serum containing the antibodies was omitted. The control is blank indicating that the fingerprint results from binding of antibodies to antigens, and not as a result of non-antibody substances binding to the antigens in the panel.

EXAMPLE IX

In this example the method of the present invention was used to screen two different blood samples to determine whether they both originated from the same individual. The same techniques and procedures were employed as described in further detail in Example 1. Both samples were reportedly from the same individual, however, one sample tested HIV positive, while the other sample tested HIV negative.

Figure 9:
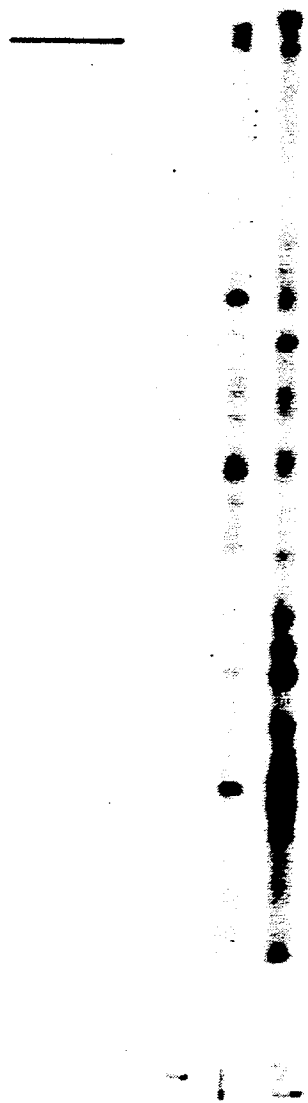
FIG. 9 shows the results of screening two samples employing the present invention to determine whether they originated from the same individual and using radioactive labeling.
Figure 10:
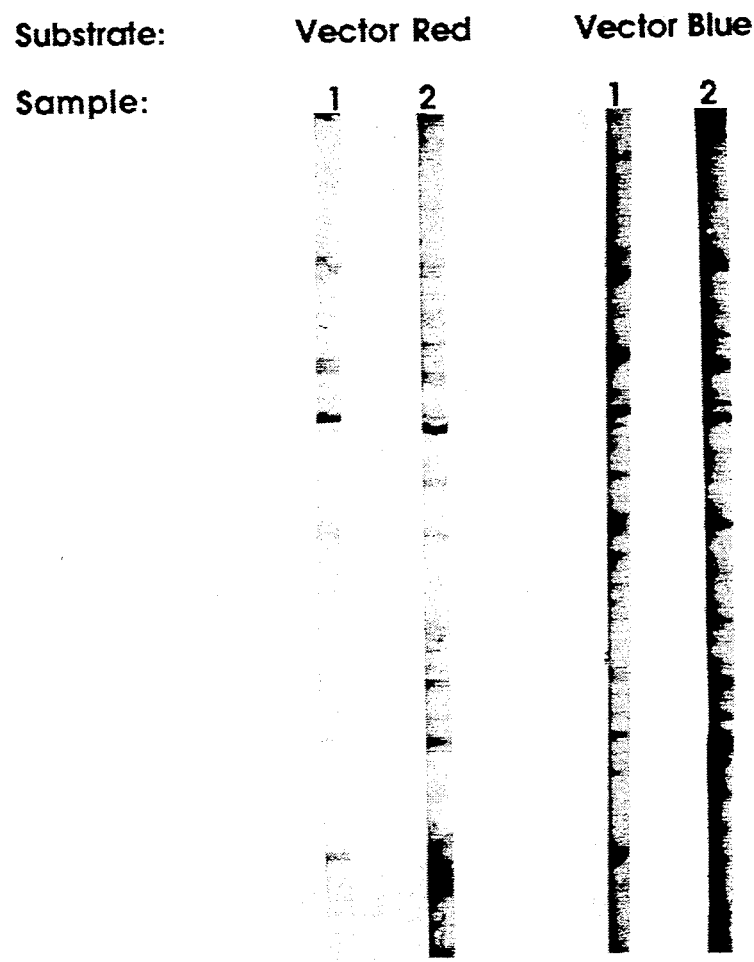
FIG. 10 shows the results of the same screenings as those shown in FIG. 9, but using colorimetric labeling.

FIG. 9 presents the data obtained using radioactive labeling as described herein. FIG. 10 presents the data employing colorimetric labeling. The samples analyzed in FIG. 9 were probed with 125-I-protein A, followed by exposure to X-ray film. The samples analyzed in FIG. 10 were probed with protein A-biotin followed by streptavidin-alkaline phosphatase. Substrates used were Vector Red and Vector Blue.

As can be appreciated from both FIG. 9 and 10, the samples were clearly obtained from two different individuals because of the numerous different bands observed.

This example illustrates the manner in which the present invention can be employed in screening without the necessity of comparing the data obtained with a known.

EXAMPLE X

Figure 11A:
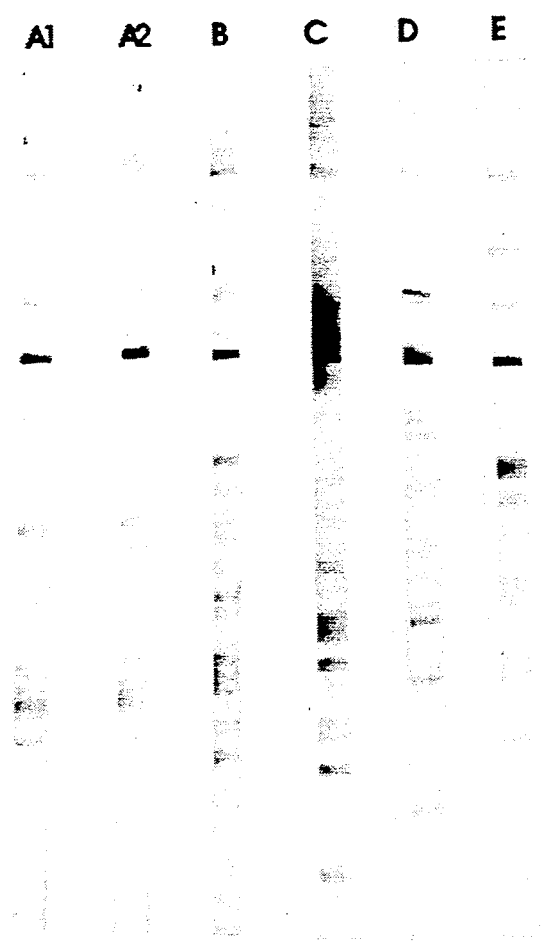
FIG. 11(a) shows the results of test samples run employing the present invention.
Figure 11B:
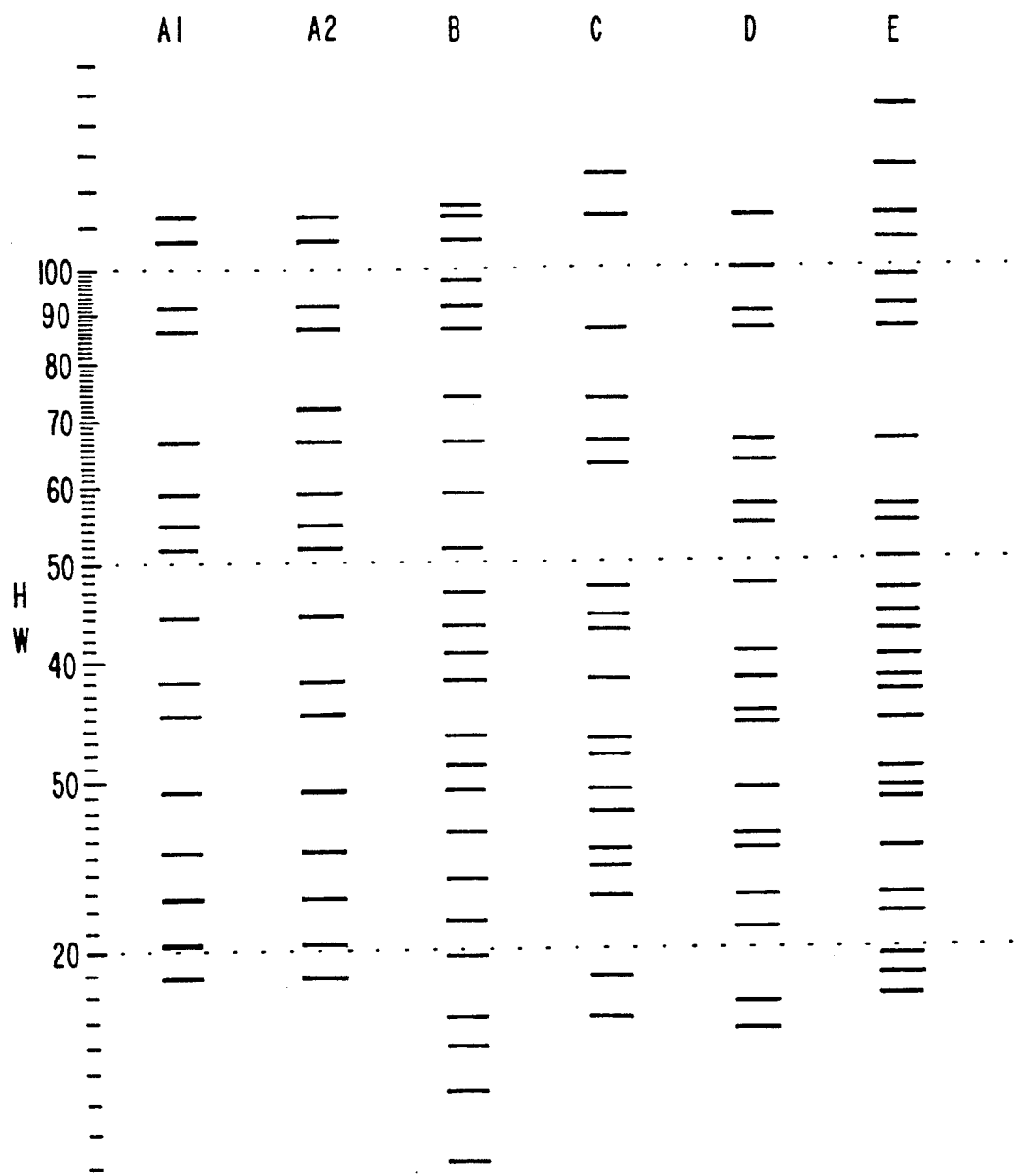
FIG. 11(6b) shows the results illustrated in FIG. 11(a) in digitized format.
FIG. 11(c) shows the results obtained from individual in FIG. 11(6b) overlaid with the results of the other individuals tested.
Figure 11C:
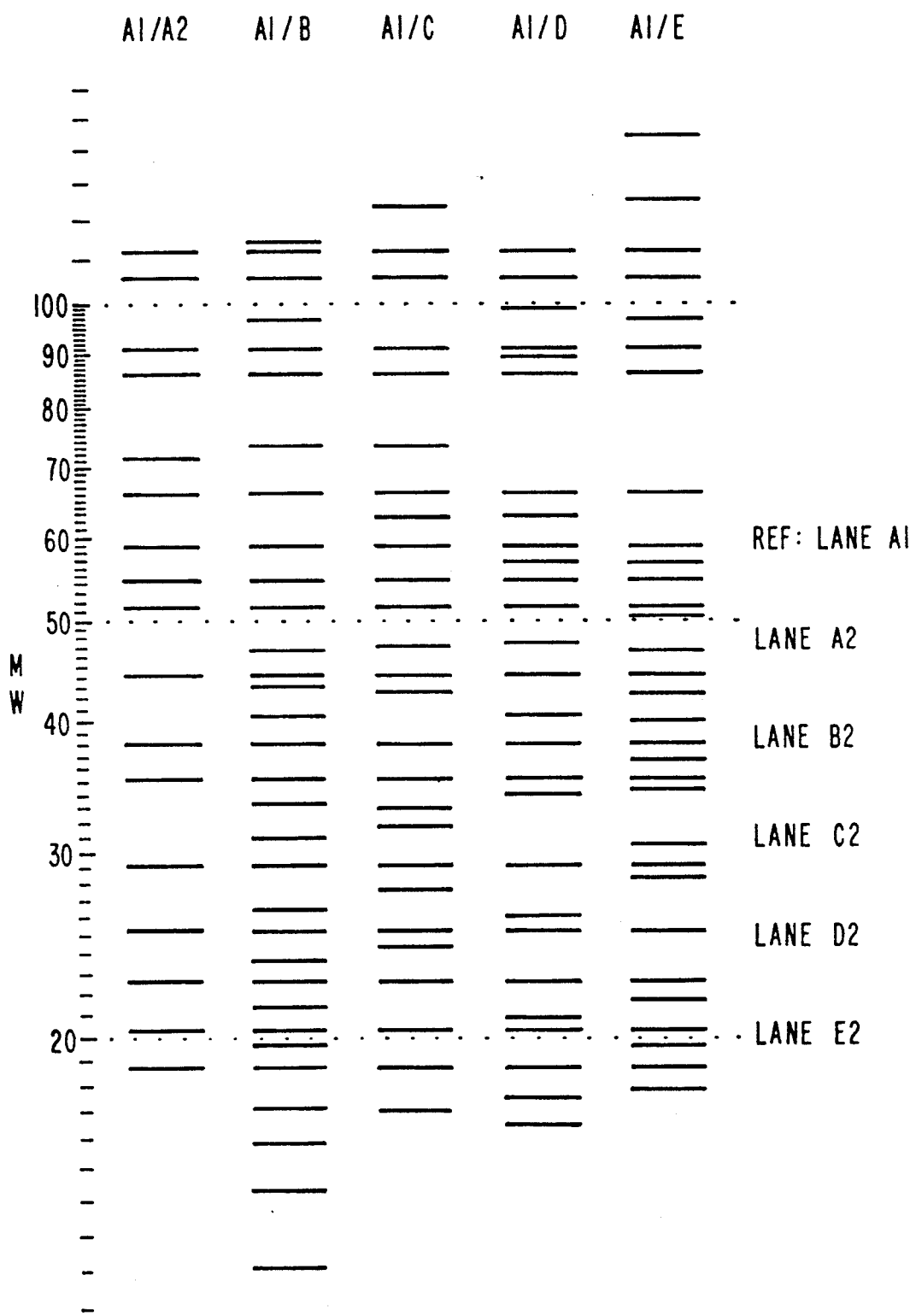

The data obtained using the present invention can be presented in the form shown in FIGS. 1-10, or it can be digitized and presented as a black-and-white or a color computer print-out. FIG. 11 shows an example of such an analysis FIG. 11(a) shows antibody fingerprints from five different individuals designated A-E. Sample A was run in duplicate (labeled A1 and A2). The strips were scanned and the black-and-white digitized results are shown in FIG. 11(6b).

The data can also be presented in color in order to aid in discrimination. For example, the original of FIG. 11(c) was colorized and shows pairwise combinations of sample A1 with A2 and B through E. Where two bands match, the color can be intermediate between that of the two used. For example, A1 was displayed in red, and A2 was blue. Where they overlap, a purple color was produced. As can be seen from FIG. 11 (c), A1 matches only A2, and not B through E.

SUMMARY

In summary, the present invention provides a method, and a kit for the performance of the method, for the identification of individuals and fluids and tissue samples originating from such individuals. The present method is extremely accurate. By obtaining the antibody profile of an individual, numerous antibodies can be analyzed. This provides a sufficient number of variables to enable precise identification and screening among and individuals and samples. Indeed, the present method can even discriminate between individuals that are genetically closely related, such as identical twins.

The method of the present invention is useful in identifying any organism that produces an antibody profile. The method is obviously useful in identifying humans, human tissue samples, and human fluid samples. The method will also find applicability in identifying a wide variety of other animals. Some such animals would include horses, especially in the context of racing or showing horses, dogs, cats and wild animals (for example, in order to identify the carrier of rabies). Trade in birds is also an important industry and the method can be used to identify such birds. In summary, the present invention is useful in identifying any animal that produces a unique antibody profile.

The present invention provides a method that is simple to perform. It is not necessary to employ complex equipment or highly trained scientists, as is the case in DNA fingerprinting and similar techniques. In addition, the present invention is operable whether or not the results are compared to a known. For example, it may be desired to determine whether a particular tissue or fluid sample originated from a particular individual. In that situation, the sample would be analyzed, as would a sample known to originate from the individual in question. In other situations it may be sufficient to determine that two samples do or do not originate from the same individual. In such a case, a simple screening procedure using the present invention is sufficient. Similarly, in other contexts it may be sufficient to sort tissue or fluid samples without the necessity of comparing any sample to a known.

It will be appreciated that the present invention is capable of being incorporated into the form of a variety of embodiments, only a few of which have been illustrated and described herein. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for identifying biological material originating from an animal capable of producing antibodies, comprising the steps of:
   (a) isolating individual-specific antibodies from a biological material;
   (b) preparing a panel of multiple antigens separated in n dimensions, where n is one or two;
   (c) forming a pattern of immune complexes of said antibodies and said antigens by contacting an effective amount of said antibodies to said panel of antigens for a time sufficient for said antibodies to bind to said antigens;
   (d) revealing said pattern of immune complexes by contacting said immune complexes with an effective quantity of antibody binding detector molecules capable of binding to said complexes; and
   (e) comparing the pattern of immune complexes with a known pattern of immune complexes, said known pattern being formed by reacting an effective amount of individual specific antibodies from a known source with a panel of multiple antigens, to determine whether the biological material tested originated from the same source as said known pattern.

2. A method for identifying biological material originating from an animal capable of producing antibodies as defined in claim 1 wherein said panel of multiple antigens is prepared from HeLa cells.

3. A method for identifying biological material originating from an animal capable of producing antibodies as defined in claim 1 wherein said detector molecules are radioactive.

4. A method for identifying biological material originating from an animal capable of producing antibodies as defined in claim 1 wherein said detector molecules are selected from the group consisting of monoclonal antibody, polyclonal antibody, and Protein A.

5. A method for identifying biological material originating from an animal capable of producing antibodies as defined in claim 1 wherein said detector molecules are preabsorbed with said panel of antigens.

6. A method for identifying biological material originating from an animal capable of producing antibodies as defined in claim 1 wherein said detector molecules produce a detectable color.

7. A method for identifying biological material originating from an animal capable of producing antibodies as defined in claim 1 further comprising the step of placing the revealed pattern of immune complexes in digitized format.

8. A method of sorting and correlating biological materials containing antibodies comprising the steps of:
   obtaining a first sample of biological material containing individual-specific antibodies;
   obtaining a second sample of biological material containing individual-specific antibodies;
   reacting the individual-specific antibodies of said first sample with a known panel of antigens to form immune complexes;
   reacting the individual-specific antibodies of said first sample with a known panel of antigens to form immune complexes:
   reacting the individual-specific antibodies of said second sample with a known panel of antigens to form immune complexes:
   revealing a pattern of immune complexes of said individual-specific antibodies from said second sample; and
   comparing the revealed pattern of complexes from said first sample with the revealed pattern of complexes from said second sample in order to determine whether said samples originated from the same source.

9. A method of sorting and correlating biological materials containing antibodies as defined in claim 8 wherein said first and second samples of biological materials are selected from the group consisting of biological fluids and biological tissues.

10. A method of sorting and correlating biological materials containing antibodies as defined in claim 8 wherein said panels are prepared from HeLa cells.

11. A method of sorting and correlating biological materials containing antibodies as defined in claim 8 wherein said revealing steps comprise contacting said immune complexes with an effective quantity of detector antibody-binding molecules.

12. A method of sorting and correlating biological materials containing antibodies as defined in claim 11 wherein said antibody-binding molecules are detectable by radioactive detection methods.

13. A method of sorting and correlating biological materials containing antibodies as defined in claim 11 wherein said antibody-binding molecules are detectable by detection methods.

14. A method of sorting and correlating biological materials containing antibodies as defined in claim 8 further comprising the step of placing said revealed patterns in digitized format.

* * * * *